United States Patent
Bradley et al.

(10) Patent No.: US 9,842,438 B1
(45) Date of Patent: Dec. 12, 2017

(54) MILEAGE AND SPEED ESTIMATION

(71) Applicant: Cambridge Mobile Telematics Inc., Cambridge, MA (US)

(72) Inventors: William Francis Bradley, Arlington, MA (US); Lewis David Girod, Arlington, MA (US); Hari Balakrishnan, Belmont, MA (US); Greg Padowski, Quincy, MA (US)

(73) Assignee: Cambridge Mobile Telematics, Inc., Cambridge, MA (US)

( * ) Notice: Subject to any disclaimer, the term of this patent is extended or adjusted under 35 U.S.C. 154(b) by 0 days.

(21) Appl. No.: 15/211,478

(22) Filed: Jul. 15, 2016

(51) Int. Cl.
| | |
|---|---|
| *G07C 5/02* | (2006.01) |
| *G01P 15/00* | (2006.01) |
| *G01H 17/00* | (2006.01) |
| *B60T 8/00* | (2006.01) |
| *G01N 19/00* | (2006.01) |
| *B60G 17/016* | (2006.01) |
| *G07C 5/08* | (2006.01) |
| *G01N 3/32* | (2006.01) |
| *E01C 19/28* | (2006.01) |
| *G01B 5/28* | (2006.01) |
| *E01C 19/22* | (2006.01) |
| *G01N 29/44* | (2006.01) |
| *G07C 5/00* | (2006.01) |
| *G06F 7/70* | (2006.01) |

(Continued)

(52) U.S. Cl.
CPC .............. *G07C 5/02* (2013.01); *G01H 17/00* (2013.01); *G01P 15/00* (2013.01); *B60G 17/016* (2013.01); *B60T 8/00* (2013.01); *E01C 19/22* (2013.01); *E01C 19/28* (2013.01); *G01B 5/28* (2013.01); *G01M 17/013* (2013.01); *G01N 3/32* (2013.01); *G01N 19/00* (2013.01); *G01N 29/44* (2013.01); *G06F 7/60* (2013.01); *G06F 7/70* (2013.01); *G07C 5/00* (2013.01); *G07C 5/08* (2013.01)

(58) Field of Classification Search
CPC ..... B60T 8/00; B60G 17/0165; B60G 17/016; B60G 17/0157; G01N 19/02; G01N 19/00; G01N 29/44; G01H 9/004; G01M 3/007; G01M 17/013; B60C 23/06; B60C 23/062; B60C 23/061; B60C 23/065; B60C 23/02; E01C 19/22; E01C 19/288; E01C 19/28; B06G 17/015; G07C 5/08; G07C 5/00; G07C 5/0808; G07C 5/008; G60G 17/0165; B66B 5/022
See application file for complete search history.

(56) References Cited

U.S. PATENT DOCUMENTS

2002/0162389 A1* 11/2002 Yokota .................... G01B 5/28
 73/105
2003/0047003 A1* 3/2003 Miyamoto ........... E01C 19/288
 73/660

(Continued)

*Primary Examiner* — Behrang Badii
(74) *Attorney, Agent, or Firm* — Occhitui & Rohlicek LLP (57) ABSTRACT

An approach to determining vehicle usage makes use of a sensor that provides a vibration signal associated with the vehicle, and that vibration signal is used to infer usage. Usage can include distance traveled, optionally associated with particular ranges of speed or road type. In a calibration phase, auxiliary measurements, for instance based on GPS signals, are used to determine a relationship between the vibration signal and usage. In a monitoring phase, the determined relationship is used to infer usage from the vibration signal.

27 Claims, 4 Drawing Sheets

(51) Int. Cl.
  *G01M 17/013* (2006.01)
  *G06F 7/60* (2006.01)

(56) References Cited

U.S. PATENT DOCUMENTS

| | | | | |
|---|---|---|---|---|
| 2004/0260436 A1* | 12/2004 | Kin | ................. | B60C 23/061 |
| | | | | 340/442 |
| 2005/0065690 A1* | 3/2005 | Ashizawa | ................ | B60K 6/48 |
| | | | | 701/51 |
| 2009/0105921 A1* | 4/2009 | Hanatsuka | ......... | B60G 17/0165 |
| | | | | 701/80 |
| 2011/0160960 A1* | 6/2011 | Kajino | ............... | B60G 17/0157 |
| | | | | 701/38 |
| 2013/0275055 A1* | 10/2013 | Hansen | ................. | G01H 9/004 |
| | | | | 702/34 |
| 2017/0084094 A1* | 3/2017 | Worden | ............... | G07C 5/0808 |

* cited by examiner

MILEAGE AND SPEED ESTIMATION

BACKGROUND

Insurance companies have a great interest in predicting the claims cost of an insured vehicle. The mileage of the vehicle is considered a useful predictor of claims cost, and is commonly estimated through odometer readings. The duration of time spent traveling at unsafe speeds can also be useful for predicting claims cost, but it is infrequently recorded.

The current methods for estimating mileage and speed suffer from several defects. One approach is to install a device into an On-Board Diagnostics (OBD) port on a vehicle thereby enabling direct acquisition of odometer and speedometer readings continuously. However, such OBD devices prone to accidental removal, can drain the vehicle's battery, and can be costly to build and operate.

Furthermore, use of a vehicle's odometer or speedometer can result in significant error. For example, overestimates of mileage based on an odometer can be 5-7% too high. Furthermore, an error or bias in an odometer reading results is a progressively greater divergence of the measured mileage from the distance actually traveled. There is no legal mandate for odometer accuracy in the USA. The European regulation is ECE-R 39, which mandates ±10% accuracy; a proposal to improve this to ±4% failed as "not practically feasible". Speedometers are relatively more accurate, but tend to overestimate speed, resulting in significant error in estimated usage of a vehicle using the speedometer reading.

GPS-enabled smartphones typically provide a more accurate measurement of distance and an estimate of speed, but require that the smartphone be present and operating consuming power.

There is a need for a new method and device to estimate mileage and speed while avoiding limitations of previous techniques.

SUMMARY

In general, an approach to determining vehicle usage makes use of a sensor that provides a vibration signal associated with the vehicle, and that vibration signal is used to infer usage. Usage can include distance traveled, optionally associated with particular ranges of speed or road type. Vibration should be understood broadly to include any motion-based phenomenon, for example, relating to position, velocity, or acceleration of a part of the vehicle (e.g, the frame, a suspension member, etc.), with the vibration signal being represented in the time domain or in the frequency domain (e.g., intensity at one or more frequencies or over a range of frequencies). In some embodiments, in a "calibration phase", auxiliary measurements, for instance based on GPS signals or other positioning approaches, are used to determine a relationship between the vibration signal and usage. In a "monitoring phase," the determined relationship is used to infer usage from the vibration signal.

In one aspect, in general, a method for determining usage of a vehicle comprises acquiring a vibration signal from a sensor of a device traveling with the vehicle. The vibration signal is processed in the device to determine a characteristic of the signal related to a use of the vehicle. The determined characteristic is then used to identify time periods during which the vehicle is in a first mode of use. Usage is accumulated in a data storage in the device. This includes accumulating a first usage for the vehicle during the identified time periods in which the vehicle is in the first mode of use. The accumulated usage is transmitted from the device.

Aspects can include one or more of the following features.

The first mode of use corresponds to travel mode. For instance, the first mode of use corresponds to travel on a first road type.

Accumulating the first usage includes accumulating at least one of a duration and a distance of travel on the first road type.

Accumulating the first usage includes accumulating a distance of travel of the first road type according to a duration of the identified time periods and an average travel speed on the first road type.

The method further comprises using the determined characteristic to identify time periods during which the vehicle is in each mode of use of a plurality of modes of use including the first mode of use. Usage of the vehicle in each mode of the plurality of modes is accumulated according to the identified time periods.

In some examples, the plurality of modes of use comprises a travel on a plurality of road types, each mode of use corresponding to a different road type. The plurality or road types can include a highway road type and/or an urban road type (e.g., a "side street" road type).

In another aspect, in general, a method for estimating motion of a vehicle makes use of a first sensor signal acquired from a sensor traveling with the vehicle. The sensor signal includes a speed related component whose characteristics depend on a traveling speed of the vehicle. The first sensor signal is processed to estimate at least one characteristic of the speed related component of the acquired sensor signal. Stored data is accessed, the accessed stored data including data associating speed of the vehicle with value of the at least one characteristic of the speed related component. The accessed data and the estimated at least one characteristic are then used to estimate the traveling speed of the vehicle.

Aspects can include one or more of the following features.

The sensor traveling with the vehicle comprises an accelerometer, which may be an accelerometer affixed to the vehicle or an accelerometer of a personal electronic device traveling with but not affixed to the vehicle. In some examples, the sensor signal comprises a multidimensional sensor signal, each dimension corresponding to a different direction relative to the vehicle.

The sensor traveling with the vehicle comprises a microphone.

The sensor signal comprises a time series (e.g., representing a time sampled or continuous waveform).

The at least one characteristic comprises a spectral characteristic. For example, the spectral characteristic characterizes frequencies of one or more energy peaks, a vibration frequency of a component of the vehicle (e.g., a tire vibration), and/or an energy distribution over frequency.

The at least one characteristic comprises a timing characteristic. For example, the timing characteristic comprises a periodicity time characteristic or an inter-event time characteristic (e.g., a time between a front wheel and a back wheel encountering a bump in the road).

The data associating speed of the vehicle with value of the at least one characteristic comprises data characterizing a statistical relationship. For example, the data comprises a data table with records, each record associating a speed of the vehicle with a value of the at least one characteristic. As another example, the data represents a linear relationship between a frequency of an energy peak and a vehicle speed.

As yet another example, the data represents an inverse relationship between an inter-event time characteristic and a vehicle speed.

The method further includes determining and storing the data associating speed of the vehicle with the one or more characteristics. A second sensor signal is acquired from a sensor (e.g., the same or a similar sensor used to acquire the first sensor signal) traveling with the vehicle and acquiring a vehicle speed signal. The second sensor signal is processed to estimate the at least one characteristic of the speed related component of the acquired sensor signal. The data associating speed of the vehicle with the at least one characteristic is determined to represent an association of the acquired vehicle speed and the estimated at least one characteristic.

Repeated estimates of the at least one characteristic over time are used to estimate speed over time, and the estimate of speed over time is used to estimate a distance traveled by the vehicle.

A drift of an speed derived from an inertial sensor according to the estimate of the traveling speed. In some examples, the sensor traveling with the vehicle used to acquire the first sensor signal is the same as the inertial sensor for which the drift is corrected.

Aspects can have one or more of the following advantages.

The approach provides increased accuracy over odometer or speedometer based approaches.

A device implementing the approach may be simpler and less expensive than OBD-based devices. Furthermore, use of such a device may be less error or failure prone than use of an OBD device.

The approach does not require ongoing use of a positioning system, for instance use of GPS.

Power requirements for a device may be relatively low, for instance, as a consequence of not requiring GPS. In some implementations, the low power requirement can enable long-term powering by an internal battery without requiring integration with a vehicle's power system. An advantage of the self-powering is that the vehicle's battery cannot be drained by the device.

Once installed, the device does not necessarily require user interaction.

Calibration and communication aspects of the system may be provided by a user's smartphone, which can be linked to the vehicle-installed device via a low-power radio (e.g., Bluetooth) link, thereby avoiding the need to implement such aspects in the device itself. However, the user's smartphone is not required on an ongoing basis is such examples.

DETAILED DESCRIPTION

Figure 1:
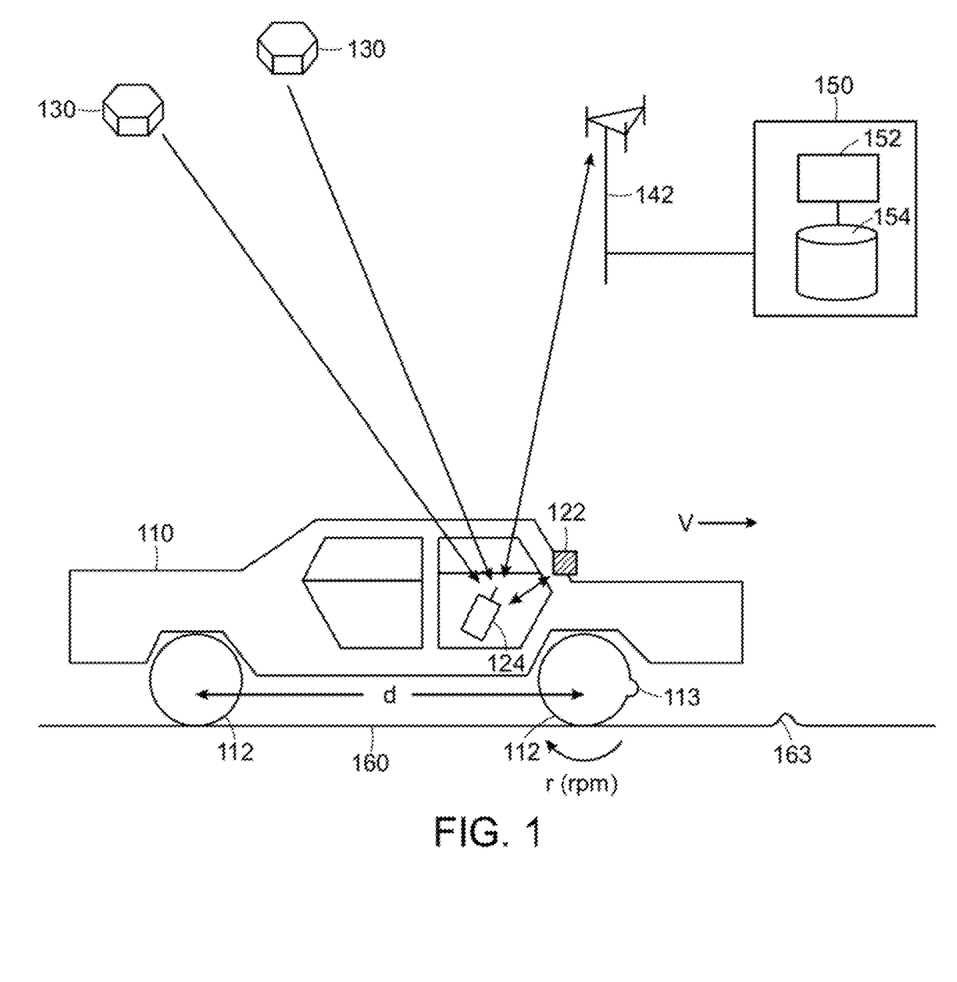
FIG. 1 is a schematic diagram representing a vehicle traveling on a roadway.

Referring to FIG. 1, a vehicle 110 is represented as traveling along the road surface 160 of a roadway at a velocity v. A tag 122 is affixed to the vehicle, for example attached to the inside of the windshield as illustrated in FIG. 1. In this embodiment, the sensor 122 is a battery-powered sensor that includes one or more accelerometers, a microprocessor, a memory, a real-time clock, and a wireless transceiver. In some embodiments, the sensor 122 is a "tag" as described in co-pending US Application "System and Method for Obtaining Vehicle Telematics Data," Ser. No. 14/529,812, published as US2015/0312655A1, which is incorporated herein by reference.

Note that although the description below focuses on use of a single tag 122 in a vehicle, in alternative embodiments there may be multiple tags on the vehicle, for example, with one tag affixed near the front wheels and another tag affixed near the rear wheels. Furthermore, in yet other embodiments, the tag may not be permanently affixed to the vehicle or the function of the tag may be incorporated into the communication device (described below).

A communication device 124, in this embodiment a cellular "smartphone" is, from time to time, in wireless communication with the tag 122 (e.g., using a low power Bluetooth protocol), whereby it is configured to receive acceleration data from the tag, either as they are acquired by the accelerometer(s) or as a batch after they have been acquired and stored in the memory of the tag. Note that the communication device 124 illustrated in FIG. 1 is not required to be present at all times because the tag 122 can operate autonomously collecting data for later transfer to the communication device 124 when it is present and communicatively coupled to the tag. The communication device 124 also receives signals from a positioning system allowing it to determine its geographic location. In this embodiment, the device 124 includes a Global Positioning System (GPS) receiver that receives and processes localization signals emitted from satellites 130 of the positioning system. The device 124 also includes a bidirectional wireless data communication transceiver, in this embodiment, that uses a cellular telephone infrastructure. The device uses this transceiver to exchange data with a remote server 150, which includes a processor 152 as well as a data storage subsystem 154.

Generally, as a supplement or a replacement to the tracking capabilities of the communication device 124 (e.g., smartphone) itself, the tag 122 provides also provides tracking capabilities. For example, when the communication device is present in the vehicle, its positioning system can be used to determine distance traveled, and when the communication device is not in the vehicle, the tag can log sufficient data to determine the distance traveled by the vehicle. Even when the communication device is in the vehicle, it may be preferable to log data with the tag rather than use the communication device's positioning capabilities in order to reduce power consumption by the communication device. For instance, a GPS receiver of a smartphone may be turned on from time to time (e.g., every 10 minutes) and the positioning information may be used in combination with the data logged by the tag in order to determine the distance and/or speed traveled by the vehicle. In some embodiments, map data is also used in combination with the tag and positioning data. Note that in the description below, generally, the tag is described separate from the communication device. In alternative embodiments, function of the tag and the communication device are combined, for example, using built-in accelerometers in the communication device. Furthermore, the tag or communication device that houses the accelerometers does not necessarily have to be firmly attached to the vehicle (e.g., in a user's pocket, in the glove-box, etc.) and the orientation of the accelerometers is inferred, for example, using the techniques described in U.S.

Pat. No. 9,228,836, "Inference of Vehicular Trajectory Characteristics with Personal Mobile Devices."

When the vehicle 110 is in motion, the tag 122 measures acceleration in one or more fixed directions relative to the vehicle's frame of reference (e.g., vertical, front-back, and side-to-side, or a rotation of these axes resulting from the orientation in which the tag is attached to the vehicle). As may be appreciated by a person with experience driving or being a passenger in a moving vehicle, the nature of a vehicle's vibration may change as the vehicle changes speed or as the nature of the road surface changes, and certain aspects of a vehicle's vibration has speed-dependent timing, for instance, as the vehicle's tires successively hit a pothole in the road surface. More generally, there are a number of factors that affect the timing, spectral content, and/or direction of vibration of a vehicle as it travels. These features of a vehicle's vibration provide information related to the vehicle's speed and the type of road surface on which the vehicle is traveling.

Figure 2:
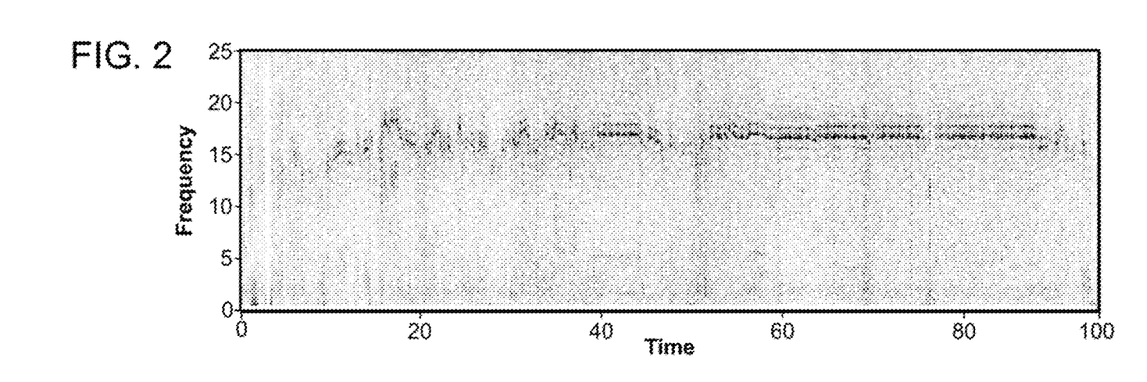
FIG. 2 is a graph of acceleration spectral density versus time.
Figure 3:
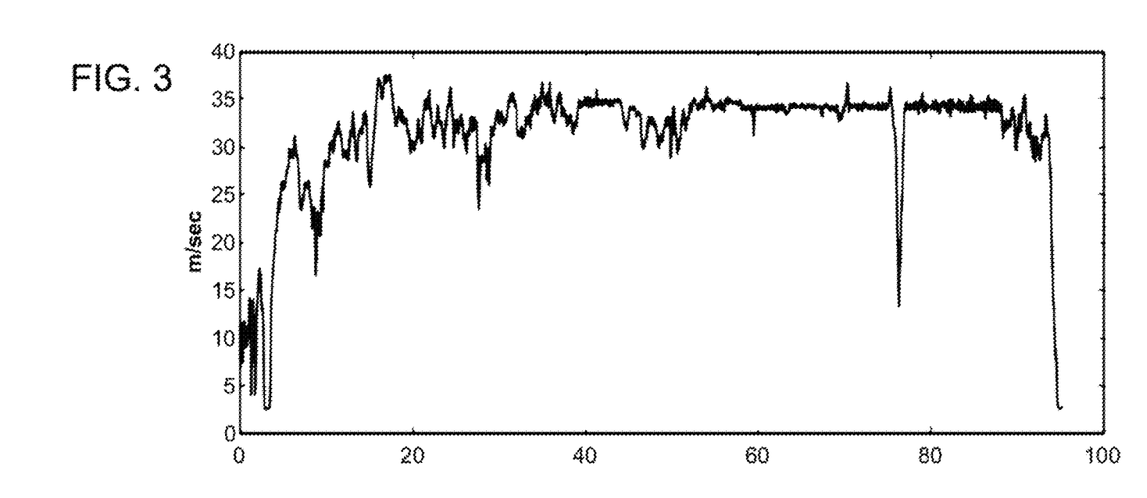
FIG. 3 is a graph of velocity versus time.

One aspect of vibration is related to the rotation speed of the vehicle's wheels, represented as r (revolutions per minute, rpm). Some mechanical characteristics of the vehicle that may cause such vibration include an faulty wheel alignment, poor tire balancing, and a tire imperfection. Also, engine vibration may relate to engine speed, which depending of the gear ratio depends on vehicle speed. Some vibration may be predominantly lateral (e.g., in some cases of faulty wheel alignment or tire imbalance), while some vibration may be largely vertical (e.g., in some cases of tire imperfection). Generally, the directional characteristic of such vibration does not change over time. Referring to FIG. 2, spectral density as a function of time is shown with higher energy being shown with increasing darkness in the figure. Referring to FIG. 3, actual vehicle speed as a function of time is shown on the same time axis as in FIG. 2. It can be seen in these figures that the actual vehicle speed tracks the spectral peak. This tracking can be understood by recognizing that a spectral peak at a frequency f (in Hertz) generally corresponds to a rotation speed of $r=f \times 60/k$, where $k \geq 1$ is an integer related to the harmonic associated with the peak.

Figure 4:
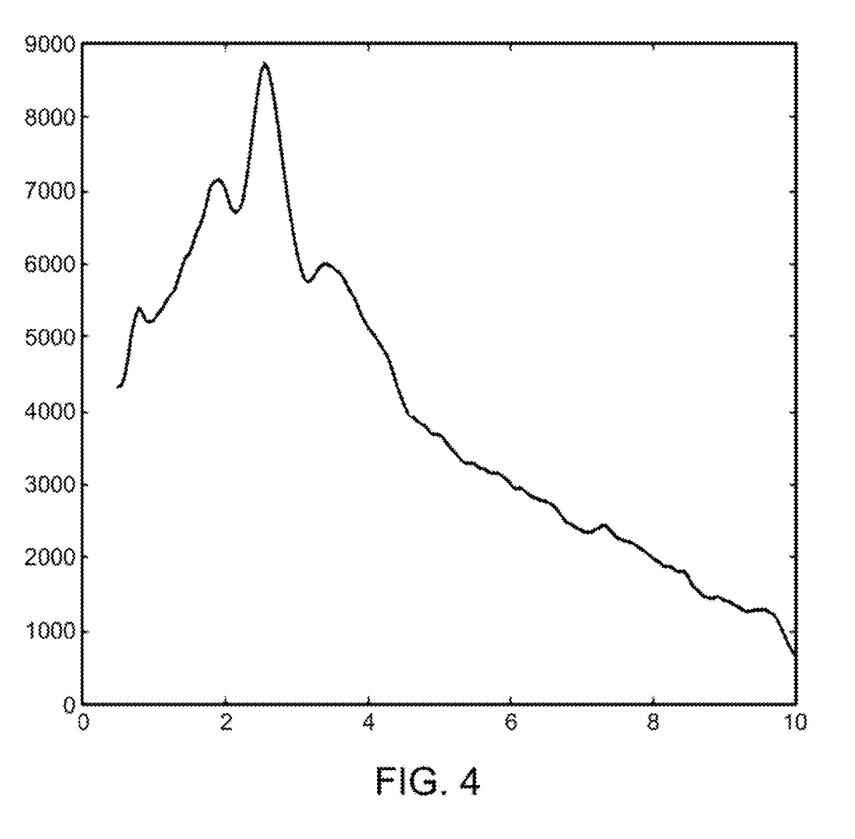
FIG. 4 is a graph autocorrelation versus wheelbase.

Yet another aspect of vibration, or more generally, an aspect of a pattern of acceleration signals, relates to successive contact between the front and then the back wheels of the vehicle and aspects (e.g, imperfections) of the road surface. As one example, as the vehicle travels along a road surface that has lateral expansion joints (e.g., as one may find on a bridge), the tag 122 will sense a vibration pattern as front wheels hit a joint and then shortly after as the rear wheel hit the same joint. If the front and rear wheels are separated by a distance d on the vehicle, and the vehicle is traveling at a speed v, then one would expect that the vibration events associated with the front and then the rear wheels would be separated in time by a duration $\tau=d/v$. The acceleration of the sensor includes components of the front wheel and the rear wheel accelerations. Therefore, when the vehicle is traveling at a fixed speed v, an autocorrelation of the acceleration signal shows a peak at delay $\tau$. During the calibration of the system, the wheelbase d can be estimated based on a known speed v as $d=\tau \times v$. In practice, the approach to estimating the wheelbase takes into account the impulse response c(t) of the vehicle, for example, related to ringing of suspension. Correlation between an acceleration signal a(t) and $a(t-d/v)-c(d/v)a(t)$ is evaluated for a range of different wheelbases d. The result is shown in FIG. 4, indicating that the estimated wheelbase is approximately d=2.55 m, which matches the true wheelbase of d=2.51 m quite accurately. Later during use, a peak of an autocorrelation at a time $\tau$ allows the system to infer that the vehicle is traveling at a speed $v=d/\tau$. This inference is performed in a set of time windows in which the vehicle speed is assumed constant for this computation.

Another aspect of vibration relates to speed and the smoothness of the road surface. For example, travel on a gravel road will cause different vibration characteristics than travel on a concrete surfaced highway. Therefore, some aspects of vibration can be used to determine when the vehicle is stopped versus in motion, and changes in engine or suspension vibration frequency or amplitude can indicate the speed that the vehicle is traveling.

As introduced above, the system can operate in a calibration phase as well as in an ongoing monitoring phase. Generally the calibration phase involves "learning" a relationship between the acquired vibration signal and vehicle motion, and the "monitoring" phase uses this relationship to estimate or otherwise infer how the vehicle has traveled.

In the calibration phase, generally, the tag acquires data generally in the same manner as it will during later monitoring. In the calibration phase, the vehicle's usage is also determined according to a secondary means. In this embodiment, the smartphone uses its GPS receiver to determine the vehicles motion, in particular, tracking its speed over time. In some examples, the smartphone also determines other characteristics of the travel, for example the road type being traveled on over time based on map information available to the smartphone based on built-in maps or information provided from a server over the data link. A relationship, for instance a statistically estimated model, between the tag-acquired data and the smartphone-determined data is then determined, for example, using a process executed in the smartphone, or alternatively on a server remote from the smartphone that receives both the tag-acquired and smartphone-determined data.

More specifically, in an example of the calibration phase, the sensor tag measures and transmits complete 3-axis acceleration data to the smartphone. The smartphone simultaneously determines speed from GPS measurements. All of these measurements are uploaded to the server. The server then breaks the acceleration data into short windows and performs a short-time Fourier transform on each window to compute the spectrogram. There are typically several spectral components in which the frequency of the largest peak in the spectrogram (in some range) varies proportionally to speed. Given this data, the relationship between the features (e.g. spectral peaks) and the speed is determined. Also, the features that do not provide information about speed are also determined so that they can be ignored. For example, certain low frequency ranges might be dominated by irrelevant information, for instance motion from a windshield wiper. The matched data allows us to detect and reject these spurious signals.

Note that since the sensor tag is in a fixed orientation relative to the vehicle, it is possible to determine this orientation and store it on the server. In the 3-axis case, the signals provide by the sensor are not necessarily aligned with standard directions such as vertical, front-back, and side-to-side. However, in the calibration phase, the server can determine a rotation of the data that yields data in the standard directions. Therefore, if there is more information in one particular direction (e.g. vertically), the server can exploit this to improve the speed estimate. The unrotated axes of the sensor tag also convey useful information, as they capture vibration perpendicular to the surface on which the sensor tag is mounted In the monitoring phase, in general, the smartphone is absent from the vehicle, or at least not necessarily in communication with the tag or tracking travel of the vehicle. The tag collects the sensor data over time. When the smartphone is next present, the stored data in the tag is uploaded to the smartphone, and from the smartphone to the server. The server then processes the uploaded data and uses the relationship between acceleration data and speed and road type to estimate the distance traveled in total and broken down by road type.

Because the acceleration data may be too large to easily store on the tag or transmit to the phone, the sensor tag in some embodiments performs a data reduction prior to transfer to the smartphone and in some embodiments prior to storage in the tag's memory. One such data reduction includes computing a short-time Fourier Transform (FT) on each axis of acceleration, and locating the largest peaks in a particular frequency range. The tag stores the index (e.g., the number of the frequency bin of the FT) and relative magnitude of the largest frequency peaks. In an alternative data reduction, the tag uses a dynamic filter to estimate the principal spectral content. By storing only the location of the spectral peaks, the data storage requirement is greatly reduced. When the smartphone is next present, these peaks are transmitted to the smartphone, which in turn transmits them to the server. The server uses the stored orientation to rotate the acceleration into the desired reference frame.

The description above focuses on determination of vehicle speed. On the other hand, the total mileage is more important for some applications. There are several alternative methods of estimating mileage. First, the speed estimates can be accumulated over time as an approximation of an integral of speed being the distance traveled. Errors in speed may cancel, producing an estimate of mileage more accurate than the constituent speed estimates.

Figure 5:
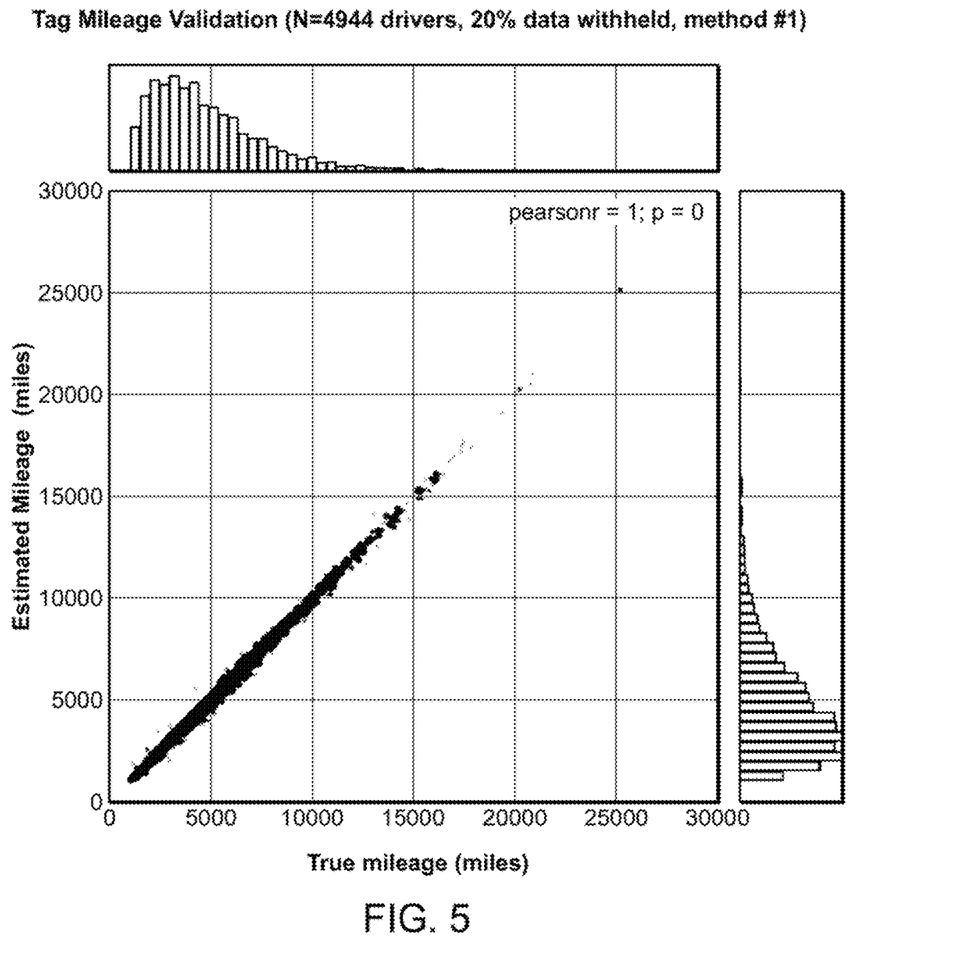
FIG. 5 is a graph predicted distance versus actual distance traveled.

The approaches described above were evaluated in experimental use in a number of vehicles. FIG. 5 shows predicted distance traveled versus the true distance traveled, with each point representing one trip, for approximately 5,000 vehicles, each taking at least 80 trips. The Pearson R value is 1.00 (to two significant digits), showing that the predicted approach provides a highly accurate estimate.

In another embodiment, the tag detects when the car is in motion by measuring when vibration levels exceed some threshold. Multiplying the duration of time that the car is in motion by the mean speed of a typical driver, the tag estimates mileage. This method requires no learning step (other than a priori knowledge of the mean speed of a typical driver). Also, the data bandwidth and memory requirements are extremely small; only the total time that the vehicle is in motion needs to be transmitted, not the underlying acceleration measurements. The accuracy of the mean speed can be improved by using collateral information, such as the driver's age.

In another embodiment, the tag is configured with the mean speed of a particular driver and multiplies this speed by the time the vehicle is in motion to yield a distance estimate. This approach requires a learning step for each driver, but might produce more accurate estimates than using a global mean driver speed. If the end user wants an estimated mileage before the learning step is complete, a global mean speed or a combination of a global and individualized mean speed can be substituted in the interim.

In another embodiment, the tag measures how frequently and for how long the vehicle stops or makes sharp turns. Vehicles on surface streets make frequent stops and sharp turns; moreover, the mean speed is relatively low. On the other hand, vehicles on highways make few stops or sharp turns and their mean speed is relatively high. The method can then produce a more accurate estimate of mileage by conditioning on vehicular stops and turns. The mean speeds can either be defined a priori based on typical driving behavior, or learned per driver.

In another embodiment, the tag keeps track of the time of day when the vehicle is driven. The method can then distinguish mileage during the day from mileage at night.

In another embodiment, the tag can keep track of the type of road (e.g., highway versus surface street) and distinguish mileage on each road type. This may be accomplished by configuring the tag with sensor signal characteristics associated with different road types, for example, provided via the smartphone after a calibration phase.

In some embodiments, the data acquired by the tag is used to infer travel along the road network. For instance, particular road segments may have characteristic sensor profiles (e.g., distinctive acceleration behavior due to the road surface). In a calibration phase, these characteristics may be match with smartphone-determined trajectory information. These profiles may be used as landmarks that are used to estimate distance traveled. In some embodiments, the characteristics may be used to match map data to infer a route traveled by the vehicle. Such matching of sensor data to a map may be augmented by using lateral and front-to-back acceleration data collected by the tag. Note that in general, the server will typically observe data from multiple vehicles. Therefore, these acceleration landmarks can be shared between vehicles, so mileage can be estimated even if a vehicle is driving somewhere it has never been before.

In some embodiments, the tag-acquired data may be compared (e.g., on the tag, the smartphone, or server) with data acquired on previous trips by the same vehicle. Because vehicles often travel the same route, some of the trips along that route may have accurate mileage estimates from the smartphone, and the acceleration features can detect matched trajectories, the method can produce much more accurate mileage estimates for those trips.

As introduced above, the tag may require relatively little power. Nevertheless, power requirements may be further reduced by cycling operation in a duty cycle, for example, in a 10% duty cycle in which data is recorded for 1 second, then the tag sleeps for 9 seconds. In that example, the total data transmission, power and memory requirements reduce by a factor of 10, but the accuracy of the mileage estimation may remain comparable to the results obtained from collecting all data.

The description above focuses on vibration measurements by a sensor tag. However, other measurements may be use in addition to or rather than vibration. For instance, the sensor signal may represent the strength of the earth's magnetic field, which may vary as the vehicle travels on the road network. Furthermore, sensing an acoustic signal may represent vibration, including speed-related phenomena such as turbulent wind noise, engine vibration and the road surface.

In some embodiments, the tag uses an accelerometer, gyroscope, or other inertial sensor to integrate distance traveled. In order to address drift of such integrated quantities, the tag uses characteristics such as spectral content, timing of successive events, etc., to correct the drift.

A variety of way of representing the relationship between the vibration data and the vehicle's speed, road type, etc. may be used. In some embodiments, this learning step uses a machine learning technique to produce a small set of nonlinear or linear features indicative of speed or mileage.

For example, the learning step trains an artificial neural net (ANN) to predict speed given acceleration data. Once trained in the calibration phase, the ANN can be used at a server to process uploaded data, or the parameters of the ANN may be downloaded to the tag or smartphone, which implements the ANN and uploads the output of the ANN, which is then used to determine the mileage estimate. In some embodiments, the ANN may contain a middle layer of reduced size, thereby implementing a data reduction. The tag can then compute the first section of the neural net and store the intermediate values from the middle layer. The smartphone can receive the intermediate values and evaluate the second half of the neural net, or upload the server and have the server evaluate the second half of the neural net. This approach would reduce memory and transmission requirements on the tag. Of course, the ANN approach is only one example. Other statistical approaches, for example, based on regression or probabilistic models can be used to represent the relationship between the data acquired or provided from the tag and the characteristics of the vehicle's travel including speed and road type.

Implementation of the approaches described above may implement the data processing steps (e.g., data storage, data reduction, and data communication) using hardware, software, or a combination of hardware and software. The hardware can include application specific integrated circuits (ASICS). The software can instructions stored on a non-transitory medium (e.g., non-volatile semiconductor memory) for causing one or more processors in the tag, the smartphone, and/or the server, to perform the procedures described above.

What is claimed is:

1. A method for determining usage of a road vehicle, the method comprising:
    acquiring a vibration signal from a sensor of a device traveling with the vehicle;
    processing the vibration signal in the device to determine a signal characteristic of the vibration signal,
        the signal characteristic including a frequency-related characteristic of the vibration signal,
        the signal characteristic depending on at least one use characteristic of the vehicle, the use characteristics including a speed of the vehicle;
    using the determined signal characteristic to determine a use characteristic of the vehicle over a plurality of time periods and to identify time periods during which the vehicle is in a first mode,
        the first mode being defined according to a speed of the vehicle;
    accumulating usage in a data storage in the device, including accumulating a first usage for the vehicle during the identified time periods in which the vehicle is in the first mode of use; and
    transmitting the accumulated usage from the device.

2. The method of claim 1 wherein the first mode of use is a non-stationary mode.

3. The method of claim 1 wherein accumulating the first usage includes accumulating at least one of a duration and a distance of travel on a first road type.

4. The method of claim 3 wherein accumulating the first usage includes accumulating a distance of travel on the first road type according to a duration of the identified time periods and an average travel speed on the first road type.

5. The method of claim 1 comprising:
    using the determined signal characteristic to identify time periods during which the vehicle is in each mode of use of a plurality of modes of use including the first mode of use; and
    accumulating usage of the vehicle in each mode of the plurality of modes according to the identified time periods.

6. The method of claim 5 wherein the plurality of modes of use comprises travel on a plurality of road types, each mode of use corresponding to a different road type.

7. The method of claim 6 wherein the plurality of road types includes at least one or a highway road type and an urban road type.

8. The method of claim 1 wherein the sensor traveling with the vehicle comprises an accelerometer.

9. The method of claim 8 wherein the sensor traveling with the vehicle comprises an accelerometer affixed to the vehicle.

10. The method of claim 8 wherein the sensor traveling with the vehicle comprises an accelerometer of a personal electronic device traveling with but not affixed to the vehicle.

11. The method of claim 8 wherein the sensor traveling with the vehicle comprises an accelerometer and the sensor signal comprises a multidimensional sensor signal, each dimension corresponding to a different direction relative to the vehicle.

12. The method of claim 1 wherein the sensor traveling with the vehicle comprises a microphone.

13. The method of claim 1 wherein the sensor signal comprises a time series.

14. The method of claim 1 wherein the signal characteristic comprises a spectral characteristic.

15. The method of claim 14 wherein the spectral characteristic characterizes frequencies of one or more energy peaks.

16. The method of claim 15 wherein the spectral characteristic characterizes a vibration frequency of a component of the vehicle.

17. The method of claim 14 wherein the spectral characteristic characterizes an energy distribution over frequency.

18. The method of claim 1 wherein the signal characteristic comprises a nonlinear or linear characteristic.

19. The method of claim 1 wherein the signal characteristic comprises a timing characteristic.

20. The method of claim 19 wherein the timing characteristic comprises a periodicity time characteristic.

21. The method of claim 19 wherein the timing characteristic comprises an inter-event time characteristic.

22. The method of claim 1 further comprising determining and storing the data associating speed of the vehicle with the one or more characteristics, the determining comprising:
    acquiring a second sensor signal from a sensor traveling with the vehicle and acquiring a vehicle speed signal;
    processing the second sensor signal to estimate the signal characteristic of the speed related component of the acquired sensor signal; and
    determining the data associating speed of the vehicle with the at least one characteristic to represent an association of the acquired vehicle speed and the estimated at least one characteristic.

23. The method of claim 1 further comprising repeating use of estimates of the characteristic over time to estimate speed over time, and combining the estimate of speed over time to estimate a distance traveled by the vehicle.

24. The method of claim 1 further comprising correcting a drift in an output of an inertial sensor according to the accumulated usage.

25. The method of claim 24 wherein the sensor traveling with the vehicle is the inertial sensor.

26. Software stored on a non-transitory machine readable medium, the software comprising instructions for causing one or more processors to:

acquire a vibration signal from a sensor of a device traveling with the vehicle;

process the vibration signal in the device to determine a characteristic of the signal related to a use of the vehicle, the signal characteristic including a frequency-related characteristic of the vibration signal and depending on a speed of the vehicle;

use the determined characteristic to identify time periods during which the vehicle is in a first mode of use, the first mode being defined according to a speed of the vehicle;

accumulate usage in a data storage in the device, including accumulating a first usage for the vehicle during the identified time periods in which the vehicle is in the first mode of use; and transmit the accumulated usage from the device.

27. A device for affixing to a vehicle, the device comprising:

a vibration sensor for providing a vibration signal;

a signal processor configured to process the vibration signal in the device to determine a characteristic of use of the vehicle, including determining a frequency-related characteristic of the vibration signal that depends on a speed of the vehicle;

a usage mode detector configured to process the determined characteristic and provide an indicator of whether the vehicle is in a first mode of use, the first mode of use being defined according to a speed of the vehicle;

a data storage for accumulating a usage for the vehicle according to time periods determined from the provided indicator; and a transmitter for transmitting the accumulated usage from the device.

* * * * *